United States Patent
Namekata et al.

(10) Patent No.: US 7,772,436 B2
(45) Date of Patent: Aug. 10, 2010

(54) PROCESS FOR PRODUCING 2,2'-BIS(TRIFLUOROMETHYL)-4,4'-DIAMINOBIPHENYL

(75) Inventors: Takeshi Namekata, Kashima (JP); Tetsuo Murata, Kashima (JP)

(73) Assignee: Air Water Inc., Sapporo-Shi, Hokkaido (JP)

( * ) Notice: Subject to any disclaimer, the term of this patent is extended or adjusted under 35 U.S.C. 154(b) by 230 days.

(21) Appl. No.: 11/666,548

(22) PCT Filed: Nov. 5, 2004

(86) PCT No.: PCT/JP2004/016403

§ 371 (c)(1),
(2), (4) Date: Apr. 30, 2007

(87) PCT Pub. No.: WO2006/048935

PCT Pub. Date: May 11, 2006

(65) Prior Publication Data

US 2009/0069602 A1   Mar. 12, 2009

(51) Int. Cl.
*C07C 211/00* (2006.01)
(52) U.S. Cl. .................. 564/307; 564/305
(58) Field of Classification Search .......... None
See application file for complete search history.

(56) References Cited

U.S. PATENT DOCUMENTS

| | | | |
|---|---|---|---|
| 1,633,123 A | 6/1927 | Nelson | |
| 1,718,373 A | 6/1929 | Nelson | |
| 4,987,258 A * | 1/1991 | Hunger et al. | 564/309 |
| 5,208,376 A | 5/1993 | Habig et al. | |

FOREIGN PATENT DOCUMENTS

| | | |
|---|---|---|
| EP | 0045459 A1 | 2/1982 |
| JP | 57-058647 A | 4/1982 |
| JP | 5-500812 A | 2/1993 |
| WO | WO 91/07377 A1 | 5/1991 |

OTHER PUBLICATIONS

R.A. Cartwright et al., "The Reactions of Certain Nitrogen-containing Compounds derived from Benzotrifluoride", Journal of Chemical Society, 1953, pp. 1994-1998, Database Crossfire Beilstein, Beilstein Institut Zur Foerderung der Chemischen Wissenschaften, Frankfurt AM Main, DE, XP002458787, Database Accession No. 402000.
S.M. Pyo et al., "Synthesis and Characterization of Fully Rodlike Poly(4,4'-biphenylene pyromellitimide)s with Various Short Side Groups", Journal of Polymer Science, Part A: Polymer Chemistry, 1999, vol. 37(7), pp. 937-957, Coden:JPACEC, ISSN: 0887-624X.
International Search Report dated Feb. 15, 2005.

* cited by examiner

*Primary Examiner*—Daniel M Sullivan
*Assistant Examiner*—Clinton Brooks
(74) *Attorney, Agent, or Firm*—Buchanan Ingersoll & Rooney PC

(57) ABSTRACT

A process for producing 2,2'-bis (trifluoromethyl)-4,4'-diaminobiphenyl which is useful as a raw material for polyimide resin, etc.
In benzidine rearrangement of 3,3'-bis(trifluoromethyl) hydrazobenzene in the presence of an inorganic acid such as sulfuric acid aqueous solution or concentrated hydrochloric acid, use of a water-immiscible organic solvent such as toluene as reaction solvent can increase the yield of the product.

3,3'-bis(trifluoromethyl) hydrazobenzene can be synthesized by reduction of m-nitrobenzotrifluoride.

4 Claims, No Drawings

PROCESS FOR PRODUCING 2,2'-BIS(TRIFLUOROMETHYL)-4,4'-DIAMINOBIPHENYL

TECHNICAL FIELD

This invention relates to a process for producing 2,2'-bis(trifluoromethyl)-4,4'-diaminobiphenyl, which are useful as a raw material for polyimide resin, etc. by benzidine rearrangement reaction from 3,3'-bis(trifluoromethyl) hydrazobenzene.

BACKGROUND

A method for producing 2,2'-bis (trifluoromethyl)-4,4'-diaminobiphenyl, that may be abbreviated as TFMB hereunder, through benzidine rearrangement reaction of 3,3'-bis(trifluoromethyl) hydrazobenzene, that may be abbreviated as hydrazo compound hereunder, is already known.

For example, according to Journal of Polymer Science Part A: Polymer Chemistry, Vol. 37, 937-957 (1999), TFMB is synthesized by dissolving the above hydrazo compound in ethanol and dropping the ethanol solution into concentrated hydrochloric acid at the temperature of 0° C. However the yield of TFMB was low level as 17 mole % based on the hydrazo compound and was insufficient as an industrial manufacturing method.

In addition, according to Journal of Chemical Society, 1994-1998 (1953), TFMB is synthesized by dissolving the above hydrazo compound in ethanol and dropping the ethanol solution of the above hydrazo compound into diluted sulfuric acid. However the yield of TFMB was only 10% by mole and therefore this was also insufficient as an industrial manufacturing method.

DESCRIPTION OF THE INVENTION

Therefore inventors have investigated the method for increasing the yield of TFMB in the rearrangement reaction from the above hydrazo compound. As a result, the inventors have reached to find that the yield can be improved by using a water-immiscible organic solvent as a reaction solvent in rearrangement reaction.

Namely, the present invention relates to a process for producing 2,2'-bis(trifluoromethyl)-4,4'-diaminobiphenyl, characterized in that the rearrangement reaction is carried out in a water-immiscible organic solvent in the presence of an inorganic acid. As the water-immiscible organic solvent, a hydrocarbon is preferable and an aromatic hydrocarbon is more preferable. As the inorganic acid, it is preferable to use diluted sulfuric acid having concentration of 10-80% by weight or concentrated hydrochloric acid. And its quantity may preferably be 1-20 moles per 1 mole of 3,3'-bis(trifluoromethyl) hydrazobenzene.

BEST EMBODIMENTS FOR THE INVENTION 3,3'-bis(trifluoromethyl) hydrazobenzene used as raw materials in the present invention may be produced by any kind of methods.

For industry, it is preferable to produce by reduction of m-nitrobenzotrifluoride directly or through 3,3'-bis(trifluoromethyl) azobenzene. As described in the above references, 3,3'-bis(trifluoromethyl) hydrazobenzene can be produced by reduction of m-nitrobenzotrifluoride using zinc or reduction of 3,3'-bis(trifluoromethyl) azobenzene using zinc or sodium amalgam. The azobenzene can be prepared by electrolytic reduction of m-nitrobenzotrifluoride.

According to the process developed by the inventors, 3,3'-bis(trifluoromethyl) hydrazobenzene can be produced directly by reducing m-nitrobenotrifluoride with zinc in the presence of an organic solvent and alkaline aqueous solution.

Explaining the process in more detail, as the organic solvent, a water-immiscible organic solvent, alcohol or a mixture thereof can be used preferably. As the water-immiscible organic solvent, there can be cited hydrocarbons, for example, aliphatic hydrocarbons such as pentane, hexane, heptane and octane, alicyclic hydrocarbons such as cycloheptane and cyclohexane and aromatic hydrocarbons such as benzene, toluene, xylene and ethyl benzene; halogenated hydrocarbons such as methylene chloride, ethyl chloride and chlorobenzene; and ethers such as diisopropyl ether and dibutyl ether. In these, it is preferable to use hydrocarbons, and especially aromatic hydrocarbons. As alcohols, it is preferable to use alcohols having 1-8 carbon atoms, preferably lower alcohols such as methanol, ethanol and propanol, and methanol and ethanol are especially preferable.

In the reduction, the mixture of water-immiscible organic solvent and alcohol can be used as solvent. In the mixed solvent, mixing ratio of water-immiscible organic solvent and alcohol are arbitrary, and alcohol ratio is preferably 0.1 to 1 parts by weight, more preferably 0.2 and 0.5 parts by weight based on 1 part by weight of the hydrocarbon. The organic solvent may be sufficiently used in the amount so that m-nitrobenzotrifluoride can be stirred effectively. Preferable amount of the organic solvent can be 1 to 20 parts by weight, more preferably 3 to 10 parts by weight based on 1 part by weight of m-nitrobenzotrifluoride.

As the alkaline aqueous solution used in the above reduction, It is preferable to use a aqueous solution of sodium hydroxide or potassium hydroxide. As the concentration of the alkaline aqueous solution, 10 to 60% by weight, especially 25 to 60% by weight, is advantageous. Further the alkaline aqueous solution can be preferably used in the amount of 0.1 to 1.0 mole, more preferably 0.25 to 0.8 moles based on 1 mole m-nitrobenzotrifluoride. In addition, zinc used in the reduction can be usually used in the amount of 2 to 10 moles, preferably 3 to 8 moles based on 1 mole of m-nitrobenzotrifluoride in consideration of both rate of reaction and economy of cost.

The reduction can be carried out under sufficient mixing of m-nitrobenzotrifluoride, the organic solvent, the alkaline aqueous solution and zinc. It is preferable to carry out the reaction in an inert gas atmosphere and under agitation. The reaction temperature can be 40 to 110° C., preferably 50 to 70° C. Although the reaction time is varying depending on reaction conditions, the time may be, for example, 4 to 6 hours.

In this invention, the rearrangement reaction of 3,3'-bis(trifluoromethyl) hydrazobenzene to 2,2'-bis (trifluoromethyl)-4,4'-diaminobiphenyl is carried out in the water-immiscible organic solvent in the presence of the inorganic acid.

As the water-immiscible organic solvent which can be used here, there can be cited hydrocarbons, for example, aliphatic hydrocarbons such as pentane, hexane, heptane and octane, alicyclic hydrocarbons such as cycloheptane and cyclohexane and aromatic hydrocarbons such as benzene, toluene, xylene and ethyl benzene; halogenated hydrocarbons such as methylene chloride, ethyl chloride and chlorobenzene; and ethers such as diisopropyl ether and dibutyl ether.

In the reaction, particularly preferred water-immiscible organic solvent is hydrocarbons, especially aromatic hydrocarbons.

In the case that 3,3'-bis(trifluoromethyl) hydrazobenzene is prepared directly by reduction of m-nitrobenzotrifluoride, it is not necessary to isolate 3,3'-bis(trifluoromethyl) hydrazobenzene from reaction mixture, and it is enough to separate the organic layer from reaction mixture and utilize it for the rearrangement reaction after easy processing. Going into details, when the water-immiscible organic solvent is used in the reduction, the organic layer separated from aqueous layer after filtrating off zinc oxide generated during the reduction can be used for the following rearrangement reaction.

When the mixed solvent of the water-immiscible organic solvent and alcohol is used as the solvent, the organic layer obtained in the same way can be used for the following rearrangement reaction after removing the alcohol from the organic layer.

Needless to say, it is possible to evaporate partially the water-immiscible organic solvent from the organic layer or to add the water-immiscible organic solvent to the organic layer in case by case.

In the case that alcohol is used as solvent in reduction, it is necessary to replace the alcohol with water-immiscible organic solvent before the rearrangement reaction.

The rearrangement reaction of 3,3'-bis(trifluoromethyl) hydrazobenzene is carried out in the water-immiscible organic solvent in the presence of the inorganic acid. As the inorganic acid, it is preferable to use sulfuric acid or concentrated hydrochloric acid, and preferably aqueous solution of sulfuric acid having concentration of 10 to 80% by weight, more preferably 20 to 60% by weight. The quantity of the inorganic acid may preferably be 1 to 20 moles, more preferably 2 to 10 moles, per 1 mole of 3,3'-bis(trifluoromethyl) hydrazobenzene. The rearrangement reaction can be carried out by dropping the solution of 3,3'-bis(trifluoromethyl) hydrazobenzene dissolved in the water-immiscible organic solvent into the inorganic acid. The dripping may be done one after another or at one time. The concentration of 3,3'-bis (trifluoromethyl) hydrazobenzene in the solution can be preferably 5-40% by weight. The reaction temperature is preferably 0 to 80° C., more preferably 5 to 50° C. The reaction time is usually 2 to 10 hours until reaction has finished.

After the reaction has finished, 2,2'-bis(trifluoromethyl)-4,4'-diaminobiphenyl can be separated as a aqueous solution of its acid salt, and recovered by treating the solution with alkaline or can be separated as insoluble acid salt, and recovered by treating it with alkaline. The obtained product can be purified to the highly pure product by re-crystallization and the like if necessary.

EXAMPLES

The present invention is explained more in detail with examples hereunder. In examples, the concentration is shown by % by weight and yield is shown by % by mole.

In addition, the analysis was conducted with high-performance liquid chromatography under the following conditions and the determination is conducted using a chemical reagent produced by Tokyo Chemical Co. Ltd., as the standard material and using external standard method.

Measurement Conditions

A column:

Intersil ODS 80A (G L science Co., Ltd. make)

Length: 250 mm, Inside diameter: 4.2 mm

Mobile Phase:

Methanol (70%)/0.1% phosphoric acid water (30%)→methanol (100%)/0.1% phosphoric acid water (0%) gradient Detector: UV (254 nm)

Example 1

In a 300 ml glass reactor equipped with a reflux condenser, a thermometry pipe and electromagnetic agitator, 20.00 g of m-nitrobenzotrifluoride and 152 g of methanol were fed under nitrogen atmosphere. 46.37 g of 40% sodium hydroxide aqueous solution was added and then 36.0 g of zinc powder was fed. Inner temperature was elevated to 65° C. and reaction was done for 5 hours at the temperature. After the reaction, a solid body was filtered off to obtain a reaction filtrate. After methanol in the filtrate was removed, the filtrate was washed with water and extracted with toluene, and then solvent was removed to obtain light yellow liquid of 16.76 g. The result of analysis of thus obtained light yellow liquid revealed that 3,3'-bis(trifluoromethyl) hydrazobenzene was separated by 96.4% yield based on m-nitrobenzotrifluoride.

4.19 g of the light yellow liquid obtained by the reduction was dissolved in 14.0 g of toluene, and the solution was dropped into 15.0 g of 50% sulfuric acid aqueous solution. The rearrangement reaction was conducted for 5 hours after the dropping. After the reaction has finished, reaction mixture was neutralized and extracted with toluene to obtain 41.4 g of toluene layer. As a result of analysis of the toluene layer, the concentration of 2,2'-bis (trifluoromethyl)-4,4'-diaminobiphenyl was 3.11%, and the yield thereof was 31.8% based on 3,3'-bis(trifluoromethyl) hydrazobenzene in the light yellow liquid obtained by the reduction. The toluene solution separated above was concentrated for crystallization. A crystallized product was recrystallized to obtain a white crystal. The result of analysis of the crystal showed that it was 2,2'-bis (trifluoromethyl)-4,4'-diaminobiphenyl having purity of 99.9% and melting point of 183° C. 2,2'-bis(trifluoromethyl)-4,4'-diaminobiphenyl was recovered by yield of 95.1% from rearrangement reaction liquid.

Example 2

In a 300 ml glass reactor equipped with a reflux condenser, a thermometry pipe and electromagnetic agitator, 20.00 g of m-nitrobenzotrifluoride and 156 g of methanol were fed under nitrogen atmosphere. 48.6 g of 40% sodium hydroxide aqueous solution was added and then 21.7 g of zinc powder was fed. Inner temperature was elevated to 65° C. and reaction was done for 5 hours at the temperature. After the reaction, a solid body was filtered off to obtain a reaction filtrate. After methanol in the filtrate was removed, the filtrate was extracted with 423 g of chloroform, and then solvent was removed to obtain light yellow liquid of 30.5 g.

Thus obtained light yellow liquid was dissolved in 190 g of acetone and 14.3 g of zinc powder was added thereto, and then 75 g of 28% ammonium chloride aqueous solution was dropped. The reaction mixture was maintained until the color has changed from yellow brown to colorless, and then dropped into 10% ammonia aqueous solution. After maintaining for 1.0 hour, the mixture was extracted by chloroform and solvents were removed from the extract to obtain light brown liquid of 17.2 g. The result of analysis of the light brown liquid showed that the purity of 3,3'-bis(trifluoromethyl) hydrazobenzene was 93.0%. This result showed that the yield was 95.5% based on m-nitrobenzotrifluoride.

5.00 g of the light brown liquid obtained by the above reduction was dissolved in 16.7 g of toluene and solution was dropped into 15.36 g of 50% sulfuric acid aqueous solution. After the dropping the rearrangement reaction was conducted for 5 hours. After the reaction has finished, reaction mixture was stayed for separating liquid layers and then 17.7 g of aqueous layer of under part was separated. The result of analysis of the aqueous layer showed that the concentration of 2,2'-bis(trifluoromethyl)-4,4'-diaminobiphenyl was 8.35% and its yield was 31.8% based on 3,3'-bis (trifluoromethyl)-4,4'-hydrazobenzene in the light brown liquid obtained by the reduction.

After the separated aqueous layer was neutralized, the aqueous layer was extracted by toluene. Extract was concentrated for crystallizing and then obtained solid body was recrystallized to obtain a white crystal. The result of analysis of the crystal showed that the crystal was 2,2'-bis (trifluoromethyl)-4,4'-diaminobiphenyl having purity 99.9% and melting point of 183° C. The product was recovered by the yield of 95.2%.

Example 3

8.71 g of the light brown liquid obtained by the reduction in Example 1 was dissolved in 29.0 g of toluene. The solution was dropped into 22.1 g of concentrated hydrochloric acid while the temperature was kept at 25° C. After the dropping, the rearrangement reaction was conducted for 3 hours at 25° C. After the reaction has finished, reaction mixture was neutralized and extracted with toluene to obtain 86.1 g of toluene layer. The result of analysis of the toluene layer showed that the concentration of 2,2'-bis(trifluoromethyl)-4,4'-diaminobiphenyl was 2.48%, and its yield was 25.4% based on 3,3'-bis(trifluoromethyl) hydrazobenzene the light brown liquid obtained by the reduction.

The toluene layer was concentrated for crystallizing and obtained solid body was recrystallized to obtain a white crystal. The result of analysis of the crystal showed that it was 2,2'-bis(trifluoromethyl)-4,4'-diaminobiphenyl having purity of 99.9% and melting point of 183° C. The product was recovered from the rearrangement reaction liquid by the yield of 95.0%.

Comparative Example 1

4.50 g of the light brown liquid obtained by the reduction same as in Example 1 was dissolved in 37.5 g of ethanol to obtain a solution. 5.53 g of concentrated hydrochloric acid was dropped into the solution at 0° C. After the dropping, rearrangement reaction was conducted for 24 hours. 50.7 g of reaction liquid was recovered and analyzed. The result of analysis showed that the concentration of 2,2'-bis(trifluoromethyl)-4,4'-diaminobiphenyl was 0.21% and its yield was 2.4% based on 3,3'-bis(trifluoromethyl) hydrazobenzene in the light brown liquid obtained by the reduction.

Comparative Example 2

4.50 g of the light brown liquid obtained by the reduction same as in Example 1 was dissolved in 26.0 g of ethanol to obtain a solution. 13.6 g of 50% sulfuric acid aqueous solution was dropped into the solution. After the dropping, the rearrangement reaction was conducted for 12 hours. 43.6 g of reaction liquid was recovered and analyzed. The result of analysis showed that the concentration of 2,2'-bis(trifluoromethyl)-4,4'-diaminobiphenyl was 0.95% and its yield was 9.5% based on 3,3'-bis(trifluoromethyl) hydrazobenzene in the light brown liquid obtained by the reduction.

INDUSTRIAL APPLICABILITY OF THE INVENTION

According to the present invention, 2,2'-bis(trifluoromethyl)-4,4'-diaminobiphenyl can produced in high yield, which can be utilized as a raw material for polyimide resin, etc. from 3,3'-bis(trifluoromethyl) hydrazobenzene.

The invention claimed is:

1. A process for producing 2,2'-bis(trifluoromethyl)-4,4'-diaminobiphenyl, which comprises that 3,3'-bis(trifluoromethyl)hydrazobenzene is rearranged by dropping a solution of 3,3'-bis(trifluoromethyl)hydrazobenzene dissolved in a water-immiscible organic solvent into an inorganic acid wherein the water-immiscible organic solvent is an aromatic hydrocarbon.

2. The process for producing 2,2'-bis(trifluoromethyl)-4,4'-diaminobiphenyl according to claim 1, wherein the inorganic acid is diluted sulfuric acid having a concentration of 10 to 80% by weight or concentrated hydrochloric acid.

3. The process for producing 2,2'-bis(trifluoromethyl)-4,4'-diaminobiphenyl according to claim 2, wherein the inorganic acid is used in an amount of 1 to 20 moles per 1 mole of 3,3'-bis(trifluoromethyl)hydrazobenzene.

4. The process for producing 2,2'-bis(trifluoromethyl)-4,4'-diaminobiphenyl according to claim 1, wherein the inorganic acid is used in an amount of 1 to 20 moles per 1 mole of 3,3'-bis(trifluoromethyl)hydrazobenzene.

* * * * *